(12) United States Patent
Bonnin

(10) Patent No.: US 9,907,665 B2
(45) Date of Patent: Mar. 6, 2018

(54) TIBIAL IMPLANT FOR KNEE PROSTHESIS

(71) Applicants: Michel Bonnin, Lyons (FR); Jan Victor, Knokke-Heist (BE)

(72) Inventor: Michel Bonnin, Lyons (FR)

(73) Assignee: Jan Victor, Knokke-Heist (BE)

( * ) Notice: Subject to any disclaimer, the term of this patent is extended or adjusted under 35 U.S.C. 154(b) by 0 days.

(21) Appl. No.: 15/094,894

(22) Filed: Apr. 8, 2016

(65) Prior Publication Data

US 2016/0296334 A1 Oct. 13, 2016

(30) Foreign Application Priority Data

Apr. 8, 2015 (FR) ...................... 15 53003

(51) Int. Cl.
*A61F 2/38* (2006.01)
(52) U.S. Cl.
CPC .................... *A61F 2/389* (2013.01)
(58) Field of Classification Search
CPC ...... A61F 2/389; A61F 2/3886; A61F 2/3868; A61F 2/30734; A61F 2002/4205; A61F 2/461
See application file for complete search history.

(56) References Cited

U.S. PATENT DOCUMENTS

| | | | |
|---|---|---|---|
| 5,964,808 A | 10/1999 | Blaha et al. | |
| 2004/0006393 A1 | 1/2004 | Burkinshaw | |
| 2010/0016976 A1 | 1/2010 | Siebel | |
| 2012/0035737 A1* | 2/2012 | Sanford | A61F 2/389 623/20.33 |
| 2013/0245777 A1 | 9/2013 | Jerry | |
| 2013/0261504 A1* | 10/2013 | Claypool | A61F 2/4657 600/587 |

* cited by examiner

*Primary Examiner* — Ann Schillinger
(74) *Attorney, Agent, or Firm* — Cantor Colburn LLP

(57) ABSTRACT

This tibial implant (2) comprises a tibial base (3) intended to be fastened to a resected proximal end of a tibia of a patient, the tibial base (3) comprising a medial bearing portion (7) and a lateral bearing portion (8); and a tibial insert (4) shaped to be mounted on the tibial base (3), the tibial insert (4) comprising a medial insert portion (17) including a concave medial bearing surface (18) intended to cooperate with a medial condyle of a femoral component or of a femur, and a lateral insert portion (19) including a concave lateral bearing surface (21) intended to cooperate with a lateral condyle of the femoral component or of the femur. The lateral insert portion (19) has, at its postero-lateral edge (24), an insert notch (26) for the passage of the tendon of the popliteus, and/or the lateral bearing portion (8) has, at its postero-lateral edge (12), a base notch (13) for the passage of the tendon of the popliteus.

15 Claims, 2 Drawing Sheets

TIBIAL IMPLANT FOR KNEE PROSTHESIS

This application is related to and claims the benefit of French Patent Application No. 15/53003 filed on Apr. 8, 2015, the contents of which are herein incorporated by reference in their entirety.

The present invention concerns a tibial implant for knee prosthesis.

A total knee prosthesis includes, in known manner, on the one hand a tibial implant comprising a tibial base intended to be fastened to the resected proximal end of the tibia of a patient, and a tibial insert intended to bear on the tibial base, and the other hand a femoral component intended to be fastened to the resected distal end of the femur and to bear on the tibial plate.

In order to limit the risks of loosening of the tibial implant and/or dislocation of the femoral component, it is known to shape the tibial base and the tibial insert so that at least one or each of these components has/have an outer profile substantially corresponding to the cortical contour of the resected proximal end of the tibia of the patient to be treated. Such a configuration of the tibial base and of the tibial insert further allows limiting the risks of conflicts with the soft tissues near the tibial implant.

In a healthy knee, the tendon of the popliteus muscle extends along and in contact with the convex postero-lateral area of the proximal end of the tibia, then along the lateral edge of the femoral lateral condyle, and finally is inserted at the bottom and in front of the lateral epicondyle of the femur, anteriorly relative to the insertion area of the lateral collateral ligament.

Consequently, even when the tibial insert has an outer profile perfectly adapted to the cortical contour of the resected proximal end of the tibia of the patient to be treated, the tibial insert is likely to come into conflict with the tendon of the popliteus muscle, and therefore to induce pain to the patient. The tibial base is also likely to come into conflict with the tendon of the popliteus muscle, and therefore induce pain to the patient, when the tibial base has a large thickness and an outer profile perfectly adapted to the cortical contour of the resected proximal end of the tibia of the patient to be treated.

In order to avoid such a conflict with the tendon of the popliteus muscle, it could be considered to undersize the tibial insert and/or the tibial base. However, such undersizing could affect the stability and/or the fastening of the knee prosthesis, and thus induce the risks of loosening and/or instability of the knee prosthesis.

The present invention aims to remedy these drawbacks.

The technical problem on which the invention is based consists therefore in providing a tibial implant for knee prosthesis which allows limiting the risks of conflict with the tendon of the popliteus, while limiting the risks of loosening and of dislocation of the knee prosthesis.

To this end, the present invention concerns a tibial implant for knee prosthesis, comprising:
- a tibial base intended to be fastened to a resected proximal end of a tibia of a patient, the tibial base comprising a medial bearing portion and a lateral bearing portion,
- a tibial insert shaped to be mounted on the tibial base, the tibial insert comprising:
  - a medial insert portion including a concave medial bearing surface intended to cooperate with a medial condyle of a femoral component or of a femur, the medial insert portion comprising a postero-medial edge and an antero-medial edge, and
  - a lateral insert portion including a concave lateral bearing surface intended to cooperate with a lateral condyle of the femoral component or of the femur, the lateral insert portion comprising a postero-lateral edge and an antero-lateral edge, characterized in that the lateral insert portion has, at its postero-lateral edge, an insert notch for the passage of the tendon of the popliteus, and/or in that the lateral bearing portion has, at its postero-lateral edge, a base notch for the passage of the tendon of the popliteus.

The presence of such a passage notch on the tibial insert and/or on the tibial base allows avoiding any risk of conflict with the tendon of the popliteus, regardless of the sizing of the tibial insert and of the tibial base. These dispositions thus allow shaping the tibial insert and the tibial base so that at least one or each of these components has an outer profile corresponding substantially to the cortical contour of the resected proximal end of the tibia of the patient to be treated, and therefore also limiting the risks of loosening and instability of the knee prosthesis.

The tibial implant may also have one or more of the following feature(s), taken alone or in combination.

According to an embodiment of the invention, the insert notch is shaped so that in conditions of use, the postero-lateral edge of the lateral insert portion extends, at said insert notch, recessed from the cortical contour of the resected proximal end of the tibia.

According to an embodiment of the invention, the insert notch is located in an angular sector centred on the intersection axis between the median antero-posterior plane and the median medio-lateral plane of the tibial insert, said angular sector including a first side oriented at an angle comprised between 20 and 40°, preferably between 25 and 35°, and for example about 30°, relative to the median antero-posterior plane of the tibial insert, and a second side oriented at an angle comprised between 60 and 80°, preferably between 70 and 80°, and for example about 80°, relative to the median antero-posterior plane of the tibial insert.

According to an embodiment of the invention, the insert notch extends from the first side to the second side of the angular sector in which the insert notch is located.

According to an embodiment of the invention, the insert notch extends over a length comprised between 5 and 10 mm.

According to an embodiment of the invention, the insert notch extends over the entire height of the tibial insert.

According to an embodiment of the invention, the antero-lateral edge of the lateral insert portion and the antero-medial edge of the medial insert portion have profiles corresponding respectively substantially to the antero-lateral and antero-medial cortical contours of the resected proximal end of the tibia.

According to an embodiment of the invention, the postero-medial edge of the medial insert portion has a profile substantially corresponding to the postero-medial cortical contour of the resected proximal end of the tibia.

According to an embodiment of the invention, the postero-lateral edge of the lateral insert portion includes a first edge portion delimiting the insert notch and at least one second edge portion, the second edge portion having a profile substantially corresponding to a respective portion of the postero-lateral cortical contour of the resected proximal end of the tibia.

According to an embodiment of the invention, the postero-lateral edge of the lateral insert portion includes a third edge portion having a profile substantially corresponding to a respective portion of the postero-lateral cortical contour of the resected proximal end of the tibia, the second and third edge portions extending on either side of the first edge portion.

According to an embodiment of the invention, the base notch is shaped so that in conditions of use, the postero-lateral edge of the lateral bearing portion extends, at said base notch, recessed from the cortical contour of the resected proximal end of the tibia.

According to an embodiment of the invention, the base notch is located in an angular sector centred on the intersection axis between the median antero-posterior plane and the median medio-lateral plane of the tibial base, said angular sector including a first side oriented at an angle comprised between 20 and 40°, preferably between 25 and 35°, and for example about 30°, relative to the median antero-posterior plane of the tibial base, and a second side oriented at an angle comprised between 60 and 80°, preferably between 70 and 80°, and for example about 80°, relative to the median antero-posterior plane of the tibial base.

According to an embodiment of the invention, the base notch extends from the first side to the second side of the angular sector in which the base notch is located.

According to an embodiment of the invention, the base notch extends over a length comprised between 5 and 10 mm.

According to an embodiment of the invention, the base notch extends over the entire height of the tibial base.

According to an embodiment of the invention, the medial bearing portion comprises a postero-medial edge and an antero-medial edge.

According to an embodiment of the invention, the antero-lateral edge of the lateral bearing portion and the antero-medial edge of the medial bearing portion have profiles corresponding respectively substantially to the antero-lateral and antero-medial cortical contours of the resected proximal end of the tibia.

According to an embodiment of the invention, the postero-medial edge of the medial bearing portion has a profile substantially corresponding to the postero-medial cortical contour of the resected proximal end of the tibia.

According to an embodiment of the invention, the postero-lateral edge of the lateral bearing portion includes a first edge portion delimiting the base notch and at least one second edge portion, the second edge portion having a profile substantially corresponding to a respective portion of the postero-lateral cortical contour of the resected proximal end of the tibia.

According to an embodiment of the invention, the postero-lateral edge of the lateral bearing portion includes a third edge portion having a profile substantially corresponding to a respective portion of the postero-lateral cortical contour of the resected proximal end of the tibia, the second and third edge portions of the postero-lateral edge of the lateral bearing portion extending on either side of the respective first edge portion.

According to an embodiment of the invention, the tibial base has an outer profile substantially identical to the outer profile of the tibial insert.

According to an embodiment of the invention, the tibial insert is shaped to be fixedly mounted on the tibial base.

According to another embodiment of the invention, the tibial insert is shaped to be movably mounted in rotation on the tibial base.

According to an embodiment of the invention, the tibial base comprises at least one fastening element, such as a fastening keel or rod, intended to be fastened to the resected proximal end of the tibia.

According to an embodiment of the invention, the tibial base is metallic.

According to an embodiment of the invention, the tibial insert is made of polyethylene, and for example of ultra-high molecular weight polyethylene.

In any case, the invention will be better understood using the following description with reference to the appended schematic drawing representing, by way of non-limiting examples, several embodiments of this tibial implant.

Figure 1:
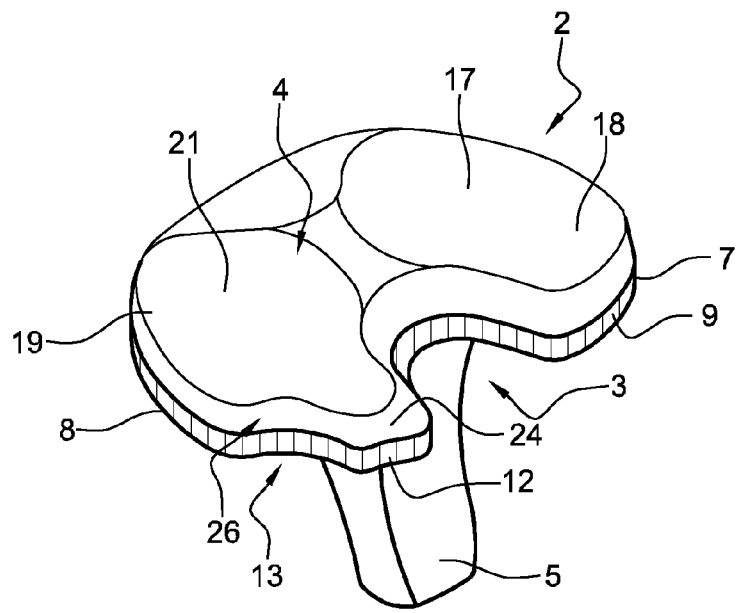
FIG. 1 is a perspective view of a tibial implant according to a first embodiment of the invention.
Figure 2:
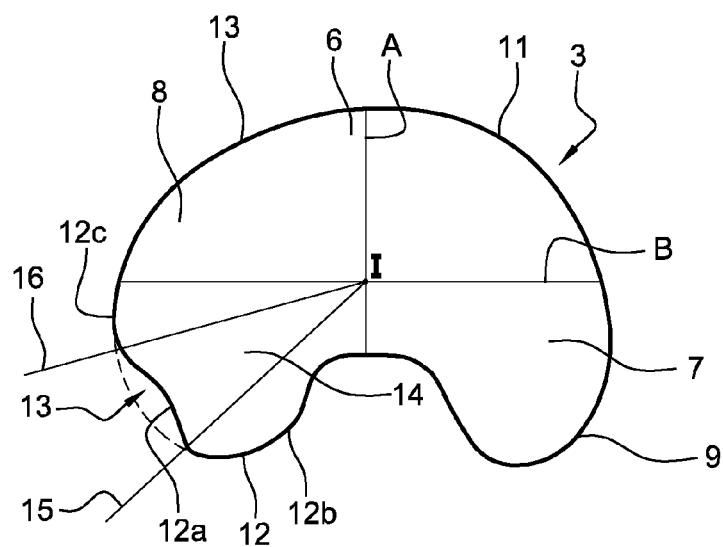
FIG. 2 is a top view of a tibial base of the tibial implant of FIG. 1.
Figure 3:
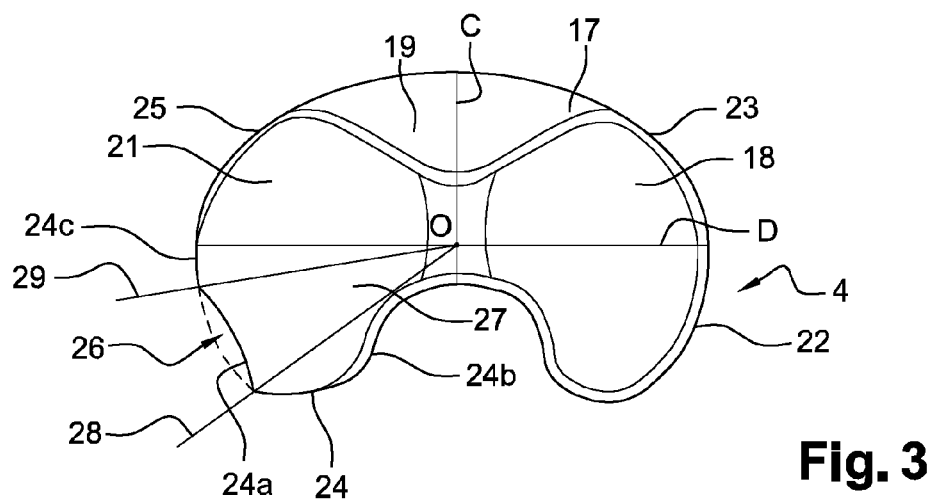
FIG. 3 is a top view of a tibial insert of the tibial implant of FIG. 1.

FIGS. 1 to 3 represent a tibial implant 2 for knee prosthesis according to a first embodiment of the invention. The tibial implant 2 comprises a tibial base 3 intended to be fastened to a resected proximal end of a tibia of a patient, and a tibial insert 4 shaped to be mounted on the tibial base 3. The tibial base may for example be metallic, and the tibial insert may be made of polyethylene, and for example of ultra-high molecular weight polyethylene.

As shown in FIG. 1, the tibial base 3 comprises at least one fastening element 5, such as a fastening keel or rod, intended to be fastened to the resected proximal end of the tibia. The tibial base 3 further comprises a bearing portion 6 intended to bear on the resected proximal end of the tibia. The bearing portion 6 comprises a medial bearing portion 7 and a lateral bearing portion 8.

The medial bearing portion 7 comprises a postero-medial edge 9 extending over a posterior portion of the tibial base 3, and more particularly from the median antero-posterior plane A, also named median sagittal plane, of the tibial base 3, to the median medio-lateral plane B, also named median frontal plane, of the tibial base 3. The medial bearing portion 7 also comprises an antero-medial edge 11 extending over an anterior portion of the tibial base 3, and more particularly from the median medio-lateral plane B to the median antero-posterior plane A.

The lateral bearing portion 8 comprises a postero-lateral edge 12 extending over a posterior portion of the tibial base 3, and more particularly from the median antero-posterior plane A to the median medio-lateral plane B. The lateral bearing portion 8 also comprises an antero-lateral edge 13 extending over an anterior portion of the tibial base 3, and more particularly from the median medio-lateral plane B to the median antero-posterior plane A.

According to the first embodiment represented in FIGS. 1 to 3, the lateral bearing portion 8 has, at its postero-lateral edge 12, a base notch 13 for the passage of the tendon of the popliteus. The base notch 13 extends over the entire height of the tibial base 3, and is located in an angular sector 14 centred on the intersection axis I between the median antero-posterior plane A and the median medio-lateral plane B. The angular sector 14 includes a first side 15 oriented at an angle advantageously comprised between 20 and 40°, preferably between 25 and 35°, and for example about 30°, relative to the median antero-posterior plane A, and a second side 16 oriented at an angle advantageously comprised between 60 and 80°, preferably between 70 and 80°, and for example about 80°, relative to the median antero-posterior plane A. The base notch 13 advantageously extends from the first side 15 to the second side 16 of the angular sector 14.

The base notch 13 is shaped so that in conditions of use, the postero-lateral edge 12 of the lateral bearing portion 8 extends, at the base notch 13, recessed from the cortical contour of the resected proximal end of the tibia. The portion of the cortical contour of the resected proximal end of the tibia extending at the base notch 13 is schematized with dotted lines in FIG. 2.

According to the first embodiment represented in FIGS. 1 to 3, the antero-lateral edge 13 of the lateral bearing portion 8 and the antero-medial edge 11 of the medial bearing portion 7 have profiles corresponding respectively substantially to the antero-lateral and antero-medial cortical contours of the resected proximal end of the tibia. The postero-medial edge 9 of the medial bearing portion 7 also has a profile substantially corresponding to the postero-medial cortical contour of the resected proximal end of the tibia.

According to the first embodiment represented in FIGS. 1 to 3, the postero-lateral edge 12 of the lateral bearing portion 8 includes a first edge portion 12a delimiting the base notch 13, a second edge portion 12b and a third edge portion 12c, the second and third edge portions 12b, 12c extending on either side of the first edge portion 12a. Each of the second and third edge portions 12b, 12c advantageously has a profile substantially corresponding to a respective portion of the postero-lateral cortical contour of the resected proximal end of the tibia. Thus, the tibial base 3 advantageously has, except at the base notch 13, an outer profile substantially corresponding to the cortical contour of the resected proximal end of the tibia.

As shown in FIGS. 1 and 3, the tibial insert 4 advantageously has an outer profile substantially identical to the outer profile of the tibial base 3. The tibial insert 4 comprises a medial insert portion 17 including a concave medial bearing surface 18 intended to cooperate with a medial condyle of a femoral component or of a femur, and a lateral insert portion 19 including a concave lateral bearing surface 21 intended to cooperate with a lateral condyle of the femoral component or of the femur. According to the embodiment represented in FIGS. 1 to 3, the tibial insert 4 is shaped to be fixedly mounted on the tibial base 3. To this end, the tibial insert 4 and the tibial base 3 include complementary fastening elements (not shown in figures) well known to those skilled in the art.

The medial insert portion 17 comprises a postero-medial edge 22 extending over a posterior portion of the tibial insert 4, and more particularly from a median antero-posterior plane C, also named median sagittal plane, of the tibial insert 4, to a median medio-lateral plane D, also named median frontal plane, of the tibial insert 4. The medial insert portion 17 also comprises an antero-medial edge 23 extending over an anterior portion of the tibial insert 4, and more particularly from the median medio-lateral plane D to the median antero-posterior plane C.

The lateral insert portion 19 comprises a postero-lateral edge 24 extending over a posterior portion of the tibial insert 4, and more particularly from the median antero-posterior plane C to the median medio-lateral plane D, and a antero-lateral edge 25 extending over an anterior portion of the tibial insert 4, and more particularly from the median medio-lateral plane D to the median antero-posterior plane C.

According to the first embodiment represented in FIGS. 1 to 3, the lateral insert portion 19 has, at its postero-lateral edge 24, an insert notch 26 for the passage of the tendon of the popliteus. The insert notch 26 extends over the entire height of the tibial base 3, and is located in an angular sector 27 centred on the intersection axis O between the median antero-posterior plane C and the median medio-lateral plane D. The angular sector 27 includes a first side 28 oriented at an angle advantageously comprised between 20 and 40°, preferably between 25 and 35°, and for example about 30°, relative to the median antero-posterior plane C, and a second side 29 oriented at an angle advantageously comprised between 60 and 80°, preferably between 70 and 80°, and for example about 80°, relative to the median antero-posterior plane C. The insert notch 26 advantageously extends from the first side 28 to the second side 29 of the angular sector 27.

The insert notch 26 is shaped so that in conditions of use, the postero-lateral edge 24 of the lateral insert portion 19 extends, at the insert notch 26, recessed from the cortical contour of the resected proximal end of the tibia. The portion of the cortical contour of the resected proximal end of the tibia extending at the insert notch 26 is schematized with dotted lines in FIG. 3.

According to the first embodiment represented in FIGS. 1 to 3, the antero-lateral edge 25 of the lateral insert portion 19 and the antero-medial edge 23 of the medial insert portion 17 have profiles corresponding respectively substantially to the antero-lateral and antero-medial cortical contours of the resected proximal end of the tibia. The postero-medial edge 22 of the medial insert portion 17 also has a profile substantially corresponding to the postero-medial cortical contour of the resected proximal end of the tibia.

According to the first embodiment represented in FIGS. 1 to 3, the postero-lateral edge 24 of the lateral insert portion 19 includes a first edge portion 24a delimiting the insert notch 26, a second edge portion 24b and a third edge portion 24c, the second and third edge portions 24b, 24c extending on either side of the first edge portion 24a. Each of the second and third edge portions 24b, 24c advantageously has a profile substantially corresponding to a respective portion of the postero-lateral cortical contour of the resected proximal end of the tibia. Thus, the tibial insert 4 advantageously has, except at the insert notch 26, an outer profile substantially corresponding to the cortical contour of the resected proximal end of the tibia.

Figure 4:
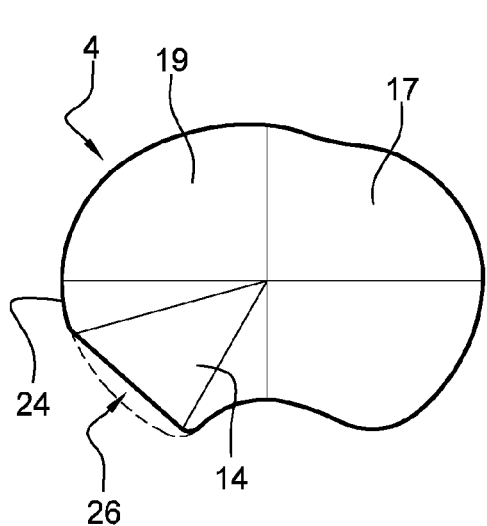
FIG. 4 is a top schematic view of a tibial insert of a tibial implant according to a second embodiment of the invention.

FIG. 4 schematically represents a tibial insert 4 of a tibial implant according to a second embodiment of the invention which differs from that represented in FIGS. 1 to 3 essentially in that the insert notch 26 is formed by a flat section. According to such embodiment of the invention, the tibial base 3 could have an outer profile substantially identical to the outer profile of the tibial insert 4 represented in FIG. 4, and thus the base notch 13 could be formed by a flat section.

Figure 5:
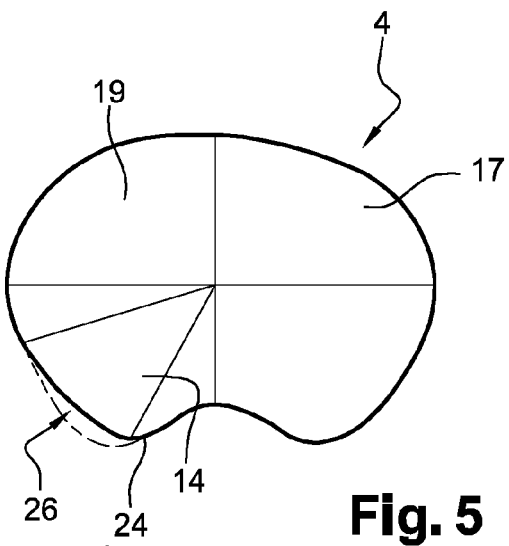
FIG. 5 is a top schematic view of a tibial insert of a tibial implant according to a third embodiment of the invention.

FIG. 5 schematically represents a tibial insert 4 of a tibial implant according to a third embodiment of the invention which differs from that represented in FIGS. 1 to 3 essentially in that the insert notch 26 is formed by a variation in the radius of curvature of the postero-lateral edge 24 of the lateral insert portion 19, and more particularly of the first edge portion 12a. According to such embodiment of the invention, the tibial base 3 could have an outer profile substantially identical to the outer profile of the tibial insert 4 represented in FIG. 5, and thus the base notch 13 could be formed by a variation in the radius of curvature of the postero-lateral edge 12 of the lateral bearing portion 8.

Figure 6:
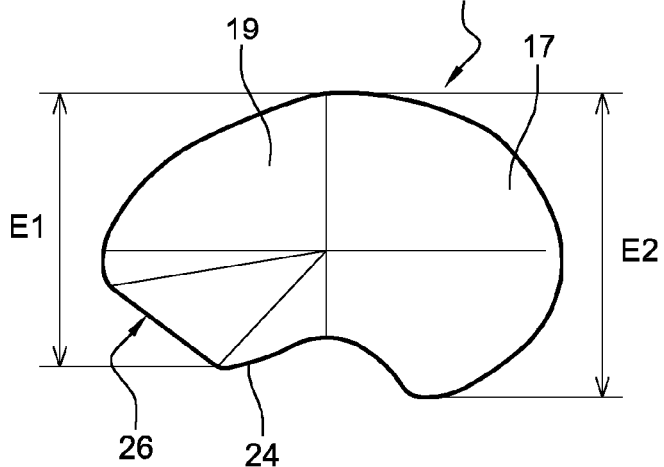
FIG. 6 is a top schematic view of a tibial insert of a tibial implant according to a fourth embodiment of the invention.

FIG. 6 schematically represents a tibial insert 4 of a tibial implant according to a fourth embodiment of the invention which differs from that represented in FIGS. 1 to 3 essentially in that the tibial insert 4 is asymmetrical, that is to say that the antero-posterior space requirement E1 of the lateral insert portion 19 is smaller than the antero-posterior space requirement E2 of the medial insert portion 17. According to such an embodiment of the invention, the tibial base 3 could have an outer profile substantially identical to the outer profile of the tibial insert 4 represented in FIG. 6, and thus the antero-posterior space requirement of the lateral bearing portion 8 could be smaller than the antero-posterior space requirement of the medial bearing portion 7.

Figure 7:
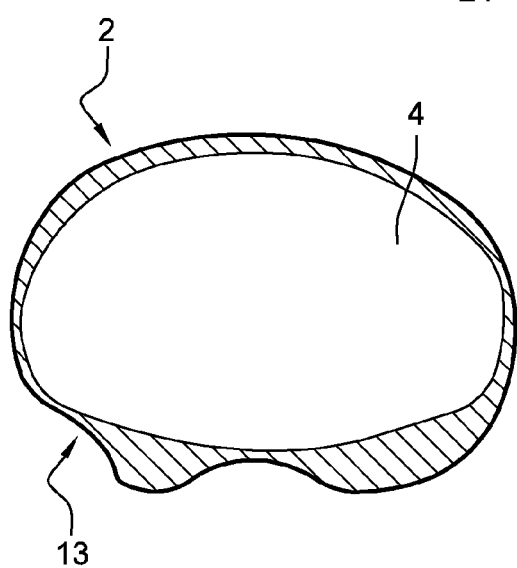
FIGS. 7 and 8 are top views of a tibial implant according to a fifth embodiment of the invention, in two different operating positions.
Figure 8:
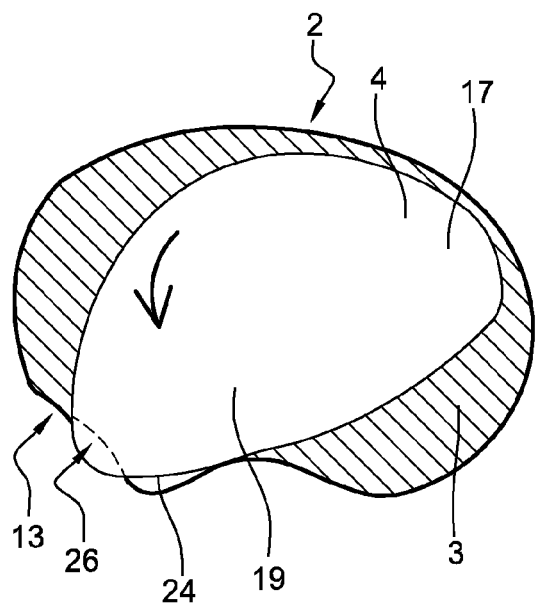

FIGS. 7 and 8 represent a tibial implant 2 according to a fifth embodiment of the invention which differs from that represented in FIGS. 1 to 3 essentially in that the tibial insert 4 is shaped to be movably mounted in rotation on the tibial base 3. To this end, the tibial insert 4 and the tibial base 3 include adapted assembling means well known to those skilled in the art.

According to such an embodiment of the invention, the tibial insert 4 could optionally be devoid of any insert notch 26. Nevertheless, in the case where the tibial insert 4 is provided with an insert notch 26 (represented with dotted lines in FIG. 8), then it is shaped so that during a maximum external rotation of the tibial insert 4, the postero-lateral edge 24 of the lateral insert portion 19 extends, at said insert notch 26, recessed from the cortical contour of the resected proximal end of the tibia.

Of course, the invention is not limited to the only embodiment of this tibial implant, described above as an example, it encompasses on the contrary all variants.

The invention claimed is:

1. A tibial implant for knee prosthesis, comprising:
a tibial base intended to be fastened to a resected proximal end of a tibia of a patient, the tibial base comprising a medial bearing portion and a lateral bearing portion, the lateral bearing portion comprising a postero-lateral edge and an antero-lateral edge,
a tibial insert configured to be mounted on the tibial base, the tibial insert being made in one piece and comprising:
a medial insert portion including a concave medial bearing surface intended to cooperate with a medial condyle of a femoral component or of a femur, the medial insert portion comprising a postero-medial edge and an antero-medial edge, and
a lateral insert portion including a concave lateral bearing surface intended to cooperate with a lateral condyle of the femoral component or of the femur, the lateral insert portion comprising a postero-lateral edge and an antero-lateral edge,
wherein the lateral insert portion has, at its postero-lateral edge, an insert notch for the passage of the tendon of the popliteus, the insert notch extending over an entire height of the tibial insert; and wherein the lateral bearing portion has, at its postero-lateral edge, a base notch for the passage of the tendon of the popliteus.

2. The tibial implant according to claim 1, wherein the insert notch is configured so that, in use, the postero-lateral edge of the lateral insert portion extends, at said insert notch, recessed from a cortical contour of the resected proximal end of the tibia.

3. The tibial implant according to claim 1, wherein the insert notch is located in an angular sector centred on an intersection axis between a median antero-posterior plane and a median medio-lateral plane of the tibial insert, said angular sector including a first side oriented at an angle comprised between 20 and 40° relative to the median antero-posterior plane of the tibial insert, and a second side oriented at an angle comprised between 60 and 80° relative to the median antero-posterior plane of the tibial insert.

4. The tibial implant according to claim 1, wherein the antero-lateral edge of the lateral insert portion and the antero-medial edge of the medial insert portion have profiles corresponding respectively substantially to antero-lateral and antero-medial cortical contours of the resected proximal end of the tibia.

5. The tibial implant according to claim 1, wherein the postero-medial edge of the medial insert portion has a profile substantially corresponding to a postero-medial cortical contour of the resected proximal end of the tibia.

6. The tibial implant according to claim 1, wherein the postero-lateral edge of the lateral insert portion includes a first edge portion delimiting the insert notch and at least one second edge portion, the second edge portion having a profile substantially corresponding to a respective portion of a postero-lateral cortical contour of the resected proximal end of the tibia.

7. The tibial implant according to claim 1, wherein the tibial base has an outer profile substantially identical to an outer profile of the tibial insert.

8. The tibial implant according to claim 1, wherein the tibial insert is configured to be fixedly mounted on the tibial base.

9. The tibial implant according to claim 1, wherein the tibial implant is a permanent tibial implant.

10. The tibial implant according to claim 1, wherein the insert notch emerges in a peripheral edge of the tibial implant.

11. The tibial implant according to claim 1, wherein the base notch is configured so that, in use, the postero-lateral edge of the lateral bearing portion extends, at said base notch, recessed from the cortical contour of the resected proximal end of the tibia.

12. The tibial implant according to claim 1, wherein the base notch is located in an angular sector centred on an intersection axis between a median antero-posterior plane and a median medio-lateral plane of the tibial base, said angular sector including a first side oriented at an angle comprised between 20 and 40° relative to the median antero-posterior plane of the tibial base, and a second side oriented at an angle comprised between 60 and 80° relative to the median antero-posterior plane of the tibial base.

13. The tibial implant according to claim 1, wherein the base notch extends over an entire height of the tibial base.

14. A tibial implant for knee prosthesis, comprising:
a tibial base intended to be fastened to a resected proximal end of a tibia of a patient, the tibial base comprising a medial bearing portion and a lateral bearing portion, the lateral bearing portion comprising a postero-lateral edge and an antero-lateral edge,
a tibial insert configured to be mounted on the tibial base, the tibial insert being made in one piece and comprising:
a medial insert portion including a concave medial bearing surface intended to cooperate with a medial condyle of a femoral component or of a femur, the medial insert portion comprising a postero-medial edge and an antero-medial edge, and a lateral insert portion including a concave lateral bearing surface intended to cooperate with a lateral condyle of the femoral component or of the femur, the lateral insert portion comprising a postero-lateral edge and an antero-lateral edge, wherein the lateral insert portion has, at its postero-lateral edge, a passage notch for the passage of the tendon of the popliteus, the passage notch being configured so that, in use, the postero-lateral edge of the lateral insert portion extends, at said passage notch, recessed from a cortical contour of the resected proximal end of the tibia; and wherein the passage notch extends over an entire height of the tibial insert and emerges in a peripheral edge of the tibial implant; and wherein the lateral bearing portion has, at its postero-lateral edge, a base notch for the passage of the tendon of the popliteus.

15. A tibial implant for knee prosthesis, comprising:

a tibial base intended to be fastened to a resected proximal end of a tibia of a patient, the tibial base comprising a medial bearing portion and a lateral bearing portion, the lateral bearing portion comprising a postero-lateral edge and an antero-lateral edge, a tibial insert configured to be mounted on the tibial base, the tibial insert being made in one piece and comprising:

a medial insert portion including a concave medial bearing surface intended to cooperate with a medial condyle of a femoral component or of a femur, the medial insert portion comprising a postero-medial edge and an antero-medial edge, and a lateral insert portion including a concave lateral bearing surface intended to cooperate with a lateral condyle of the femoral component or of the femur, the lateral insert portion comprising a postero-lateral edge and an antero-lateral edge, wherein the lateral insert portion has, at its postero-lateral edge, an insert notch for the passage of the tendon of the popliteus, the insert notch extending over an entire height of the tibial insert, wherein the lateral bearing portion has, at its postero-lateral edge, a base notch for the passage of the tendon of the popliteus, the base notch being located in an angular sector centred on an intersection axis between a median antero-posterior plane and a median medio-lateral plane of the tibial base, said angular sector including a first side oriented at an angle of about 30° relative to the median antero-posterior plane of the tibial base, and a second side oriented at an angle of 70° relative to the median antero-posterior plane of the tibial base.

* * * * *